United States Patent [19]
Itose et al.

[11] Patent Number: 6,067,158
[45] Date of Patent: May 23, 2000

[54] METHOD FOR DETECTING ABNORMAL MORPHOLOGY OF ERYTHROCYTES

[75] Inventors: Yuji Itose; Kayo Hatanaka; Tomohiro Sakurai, all of Hyogo-ken, Japan

[73] Assignee: Sysmex Corporation, Kobe, Japan

[21] Appl. No.: 09/067,296

[22] Filed: Apr. 27, 1998

[30] Foreign Application Priority Data

May 2, 1997 [JP] Japan .................................. 9-114568

[51] Int. Cl.⁷ .................................................. G01N 21/00
[52] U.S. Cl. ........................................ 356/340; 356/341
[58] Field of Search ............................ 356/340, 39, 244, 356/246, 337, 338, 341; 435/1.4, 5; 436/8, 10, 15, 17, 18, 63

[56] References Cited

U.S. PATENT DOCUMENTS

| | | | |
|---|---|---|---|
| 3,705,771 | 12/1972 | Friedman et al. ........................ | 356/39 |
| 4,412,064 | 10/1983 | Hinman ...................................... | 528/9 |
| 4,575,490 | 3/1986 | Ornstein et al. ........................... | 436/63 |
| 4,735,504 | 4/1988 | Tycko ........................................ | 356/336 |
| 5,284,771 | 2/1994 | Fan et al. .................................. | 436/10 |
| 5,633,167 | 5/1997 | Fan et al. .................................. | 436/17 |

FOREIGN PATENT DOCUMENTS 3-57423  4/1986  Japan .

*Primary Examiner*—Frank G. Font
*Assistant Examiner*—Michael P. Stafira
*Attorney, Agent, or Firm*—Pearne, Gordon, McCoy & Granger LLP

[57] ABSTRACT

A method for detecting abnormality in the morphology of erythrocytes, which comprises:

(1) mixing a sample containing erythrocytes with a sphere-forming reagent;

(2) introducing the sample treated in the preceding step into a detector area of a flow cytometer;

(3) measuring at least one scattered light at an angle reflecting the morphology of erythrocyte among the scattered lights emitted from the sample to obtain cell distribution data; and (4) comparing the cell distribution data with cell distribution data on normal erythrocytes that were determined beforehand.

7 Claims, 6 Drawing Sheets

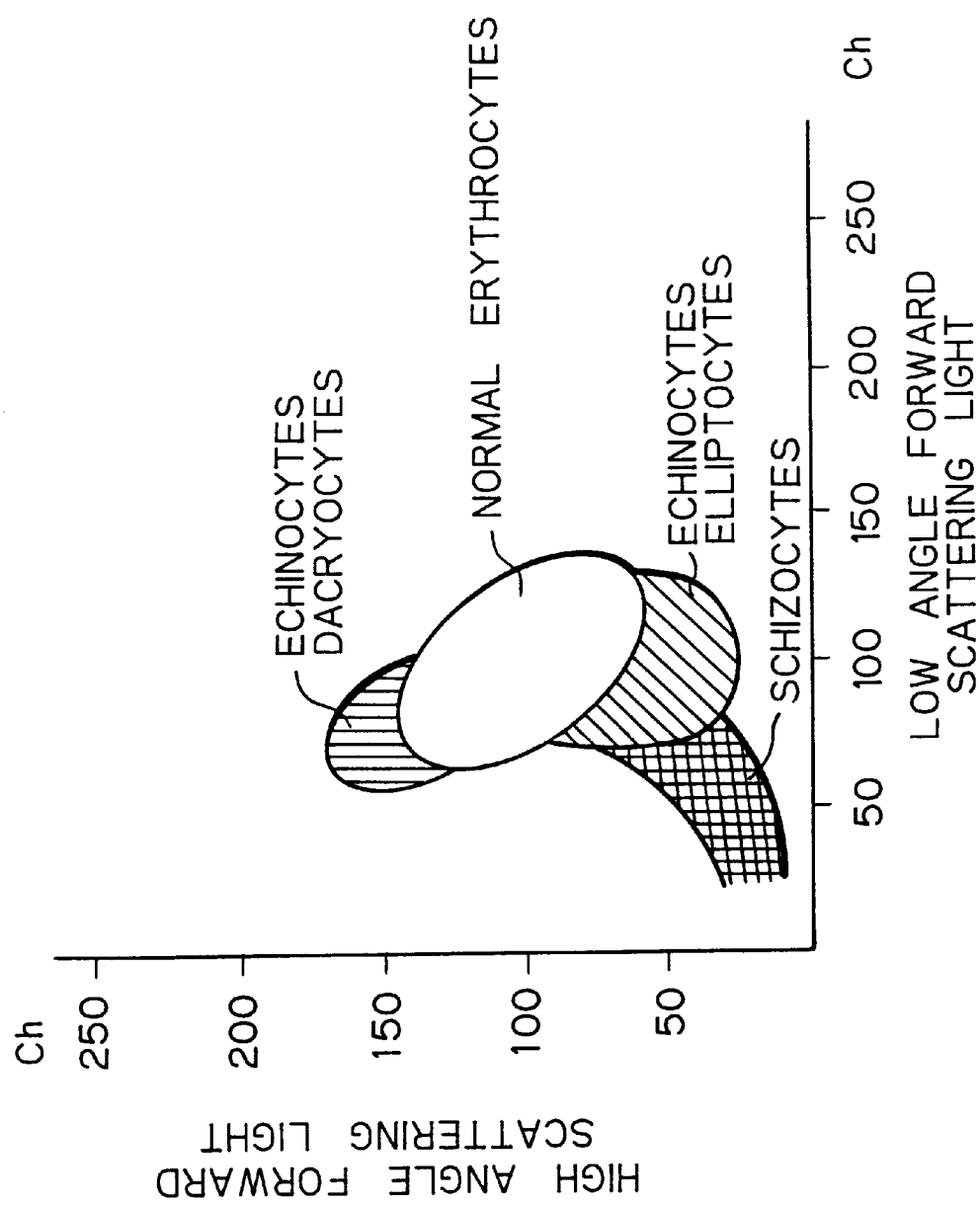

METHOD FOR DETECTING ABNORMAL MORPHOLOGY OF ERYTHROCYTES

BACKGROUND OF THE INVENTION

This invention relates to a method for detecting abnormal morphology of erythrocytes by the use of optical means.

Observing the morphology of erythrocytes in the blood is useful for obtaining valuable information for diagnosis of various diseases. Elliptocytes, for example, are noted in hereditary elliptocytosis, iron deficiency anemia and megaloblastic anemia. Echinocytes mostly occur after blood sampling, but are observed rarely in uremia. Dacryocytes are seen in myelofibrosis, myelic metastasis of cancer, and thalassemia. Schizocytes appear in DIC (disseminated intravascular coagulation), uremia, and microvascular hemolytic anemia. Anisocytosis develops in various anemias. Other abnormal forms of erythrocyte include sickle cell, holly leaf form, etc.

Various blood cell counters are commercially available now. Their principles of counting are roughly classified into the electric resistance system and the optical system. A number of automatic blood cell counters can not only count blood cells, but also measure the hemoglobin concentration. They are also able to supply information on the particle size distribution of blood cells. Some counters determine whether blood samples are normal or abnormal, by the measurements of these plural parameters in accordance with the determination equation. Based on the determinations, these counters display an abnormality message in case of abnormal findings, or a suspect message if any disease or abnormality is suspected.

Messages from blood cell counters that show abnormalities in the red cell system are merely concerned with abnormalities in the count, abnormalities in the size, and abnormalities in the hemoglobin concentration of erythrocytes. When MCHC (mean cell hemoglobin concentration) exceeds 36.5 g/dl, spherocytosis is suspected. If the particle size distribution intermediate between erythrocytes and thrombocytes is abnormal, the appearance of schizocytes is suspected. Other states of abnormal morphology cannot be suggested by suspect messages issued based on the measurements.

SUMMARY OF THE INVENTION

An object of the present invention is to provide a method for easily detecting the abnormal morphology of erythrocytes, which has thus far been undetectable, by means of a flow cytometer.

We, the inventors, have conducted extensive studies, and found that when made into a spherical form, erythrocytes with abnormal morphology show light scattering characteristics different from those of normal erythrocytes. This finding has led us to accomplish the present invention.

In detail, the present invention is characterized by detecting abnormality in the morphology of erythrocytes, which comprises:

(1) mixing a sample containing erythrocytes with a sphere-forming reagent;

(2) flowing the sample treated in the preceding step into a flow cytometer;

(3) measuring at least scattered light at an angle reflecting the morphology of erythrocytes among the scattered lights emitted from the sample to obtain cell distribution data; and (4) comparing the cell distribution data with cell distribution data on normal erythrocytes that were determined beforehand.

Abnormal morphologies of erythrocyte referred to in the present invention include states as described in William, J. et al.: Hematology, 4th Ed., pp. 310–311, McGraw-Hill, New York, 1990, namely, elliptocyte, echinocyte, dacryocyte, schizocyte, anisocytotic erythrocyte, sickle cell, and holly leaf form.

BRIEF DESCRIPTION OF THE DRAWINGS

FIG. 13 is a schematic representation of a low angle forward scattering-high angle forward scattering scattergram of abnormal erythrocyte morphologies.

DETAILED DESCRIPTION OF THE PREFERRED EMBODIMENTS

Figure 1:
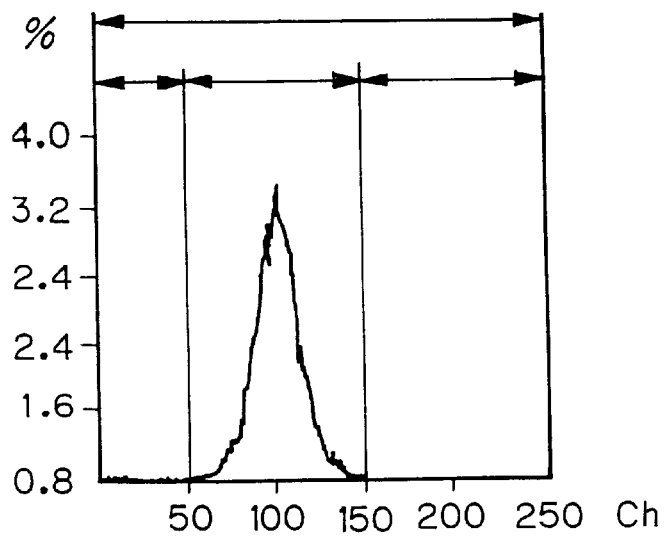
FIG. 1 is a high angle forward scattering histogram of a normal sample.

The sphere-forming reagent used in the present invention may contain a surfactant in an amount effective for making erythrocytes spherical. The surfactant is not restricted unless it lyses erythrocytes. Cationic surfactants, anionic surfactants, nonionic surfactants, and amphoteric surfactants may be used as the surfactant. If the surfactant used alone causes lysis of erythrocytes, a fixing agent such as an aldehyde, for example, formaldehyde or paraformaldehyde, may be contained in a concentration which does not impede the formation of erythrocytes into spheres, e.g., a concentration in the range of 0.3 to 3 g/dl.

Preferred examples of the cationic surfactant are quaternary ammonium salts having the following structural formula:

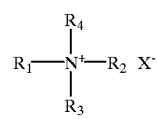

where $R_1$ designates a $C_{10-16}$ alkyl group, $R_2$, $R_3$ and $R_4$ each designate —H or a lower alkyl group, and X designates a halogen atom.

As the nonionic surfactant, those having the following structural formula may be used:

where $R_1$ designates a $C_{8-18}$ alkyl group, and n denotes 8 to 18.

As the anionic surfactant, an alkylsulfuric acid metal salt, such as sodium dodecyl sulfate, is particularly preferred.

As the amphoteric surfactant, an alkylbetaine and an alkylamidobetaine are preferred. Their examples include lauramidopropylbetaine, N-tetradecyl-N,N-dimethyl-3-ammonio-1-propanesulfonate, N-dodecyl-N,N-dimethyl-3-ammonio-1-propanesulfonate, cocoamidopropylbetaine, and cocoamidosulfobetaine. They are described in Japanese Patent Publication Nos. 3-57423, 3-46784 and 4-62339 and Japanese Unexamined Patent Publication No. 6-180316.

Particularly useful as the surfactant are the cationic surfactants, of which those having the following structure are preferred:

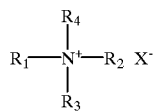

where $R_1$ designates a $C_{8-12}$ alkyl group, $R_2$, $R_3$ and $R_4$ may be the same or different, and each designate a lower alkyl group, and X designates a halogen atom.

In the $C_{8-12}$ alkyl group, a linear or branched alkyl group is included. Its examples are an octyl group, a decyl group and a lauryl group, of which octyl and decyl are preferred.

Examples of the lower alkyl group are a methyl group, an ethyl group, a propyl group and an isopropyl group.

Specific examples of the cationic surfactant are octyl trimethylammonium bromide (OTAB), decyl trimethylammonium bromide (DTAB) and lauryl trimethylammonium chloride (LTAC).

The concentration of the cationic surfactant used depends on the total carbon number of $R_1$ to $R_4$. As the total carbon number increases, the concentration of the cationic surfactant that proves effective may be low.

For instance, the preferred concentration is 300 to 20,000 mg/l for OTAB, 30 to 5,000 mg/l for DTAB, or 10 to 500 mg/l for LTAC. A further preferred concentration is 4,000 to 10,000 mg/l for OTAB, 200 to 3,000 mg/l for DTAB, or 30 to 300 mg/l for LTAC. Too large an amount of the cationic surfactant is undesirable, because erythrocytes are so damage that their hemolysis may be caused.

The sphere-forming reagent may further contain a buffer for maintaining a constant pH. The buffer is used in a concentration of several millimols to about 100 mM. The type of the buffer is not restricted, as long as it is used usually. For example, carboxylates, phosphates, Good's buffer, taurine, or triethanolamine can be used suitably depending on the desired pH. The preferred pH of the reagent in the present invention is in the range of 6.0 to 11.0, preferably 7.0 to 10.0, and more preferably 8.0 to 9.5. A pH much lower or higher than this range is not preferred, since erythrocytes will become fragile and apt to hemolyze.

Furthermore, an osmotic pressure compensator may be contained. The osmotic pressure should desirably be adjusted to physiological osmotic pressure so that the hypotonic hemolysis of erythrocytes will be prevented. Normally, the osmotic pressure is adjusted to 150 to 600 mOsm/kg. The osmotic pressure compensator is not restricted, but preferred examples are alkali metal salts of propionic acid, etc., and saccharides such as glucose and mannose. Alkaline metal halides such as NaCl, and alkaline earth metal halides are also usable. Polyvalent anions can also be used. Suitable examples of the polyvalent anions are sulfate ions, phosphate ions, carbonate ions, and polycarboxylate ions. Compounds capable of supplying them are, for example, citric acid, sulfuric acid, phosphoric acid, EDTA and alkaline metal salts thereof.

When the buffer is able to maintain an osmotic pressure suitable for measurement, the buffer can also serve as the osmotic pressure compensator.

In addition to the above-described constituents, the sphere-forming reagent may contain preservatives, such as sodium 2-pyridylthio-1-oxido, β-phenethyl alcohol, BIT (benzisothiazolone), and triazines, in order to prevent the multiplication of bacteria during storage. The method of the present invention is described below with reference to FIG. 1A. The steps of the method are summarized in the four blocks of the diagram of FIG. 1A beginning at the top thereof and discussed in detail below.

To carry out the present invention, a sample containing erythrocytes and a sphere-forming reagent are mixed in the step (1) to prepare an assay sample. The erythrocyte-containing sample may be either anticoagulant-treated peripheral blood, or blood diluted with a diluent such as physiological saline solution. In preparing the assay sample, it is preferred to mix the erythrocyte-containing sample and the sphere-forming reagent at a ratio of 1:100 to 1:1,000 and react them with each other. The reaction temperature is preferably 25 to about 50° C., and more preferably 35 to 45° C. The reaction time is preferably 10 seconds to about 5 minutes, more preferably 20 seconds to about 2 minutes, most preferably 20 to about 60 seconds.

In the step (2), the assay sample obtained in the step (1) is introduced into a detector area of a flow cytometer. The light source is not restricted, as long as it can be used in the flow cytometer. A known illuminator such as an argon laser, an He-Ne laser, or a semiconductor laser can be used.

Then, in the step (3), at least one scattered light at an angle reflecting the morphology of an erythrocyte is measured to obtain scattered light intensity distribution data. The angle reflecting the morphology of the erythrocyte is, for example, such that the angle for detection of the scattered light is in the range of 8 to 20 degrees or 70 to 110 degrees to the optical axis.

In the step (4), the measured data obtained in the step (3) are compared with cell distribution data on a normal sample that were determined beforehand.

In the present invention, it is permissible to measure not only the scattered light at an angle reflecting the morphology of erythrocyte, but also scattered light at an angle reflecting the size of the erythrocyte. Based on the measurements, a two-dimensional scattergram is prepared, and this diagram is compared with data on normal erythrocytes, whereby abnormal morphology of sampled erythrocytes can be detected. In this case, the angle reflecting the size of erythrocyte is in the range of 1 to 6 degrees to the optical axis. Thus, the two-dimensional scattergram can be prepared, for example, by either setting the first angle at 8 to 20 degrees and the second angle at 1 to 6 degrees, or setting the first angle at 70 to 110 degrees and the second angle at 1 to 6 degrees.

Alternatively, a fluorescent dye which can stain reticulocytes is incorporated in the sphere-forming reagent. The fluorescent dye-containing reagent is mixed with a sample containing erythrocytes, and the mixture is introduced into the detector area of a flow cytometer. Fluorescence generated by the assay sample and scattered light at an angle reflecting the morphology of erythrocyte are measured to prepare a two-dimensional scattergram. This diagram is compared with data on normal erythrocytes, whereby abnormal morphology of sampled erythrocytes can be detected. As the fluorescent dye capable of staining reticulocytes, a basic fluorescent dye, such as flavophosphine-R, coriphosphine-O, 4-(4'-diethylaminostyryl)-N-methylpyridinium iodide, acridine orange, or pyronine-G, can be used.

The data on normal erythrocytes can be determined by measuring an effective number of normal samples for establishing the normal sample region, say, 30 or more normal samples, and setting the borderline values from the distribution data obtained. The borderline values can be set experimentally or by a statistical method using the mean values of the distribution, standard deviations, and so on.

The detection of abnormal morphology can be performed, in the case of the particle size distribution data indicated by the scattered light histogram, by monitoring whether or not the distribution data spread outside the normal range, whether or not the width of the distribution goes beyond the normal range, or whether or not the distribution has a single peak. For the two-dimensional scattergram, a particular region is preset, and when the data appear in this region, the data can be detecting as representing abnormal morphology.

So doing is still insufficient to classify abnormalities in morphology by type, but makes it possible to detect abnormal morphology which has been undetectable by conventional methods.

The present invention will now be described in more detail by, but not restricted to, the following Embodiments:

Composition of sphere-forming reagent

| | |
|---|---|
| Tricine | 10 mM |
| Trisodium citrate | 100 mM |
| NaHCO$_3$ | 10.5 mM |
| Na$_2$CO$_3$ | 9.5 mM |
| DTAB (cationic surfactant) | 1,000 ppm |
| pH | 9.0 |
| Osmotic pressure | 340 mOsm/kg |

Setting of normal range

Figure 2:
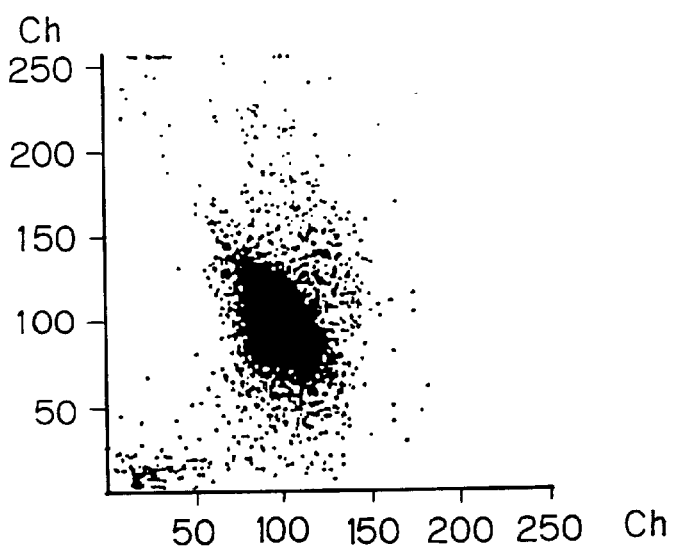
FIG. 2 is a low angle forward scattering-high angle forward scattering scattergram of a normal sample.
Figure 1A:
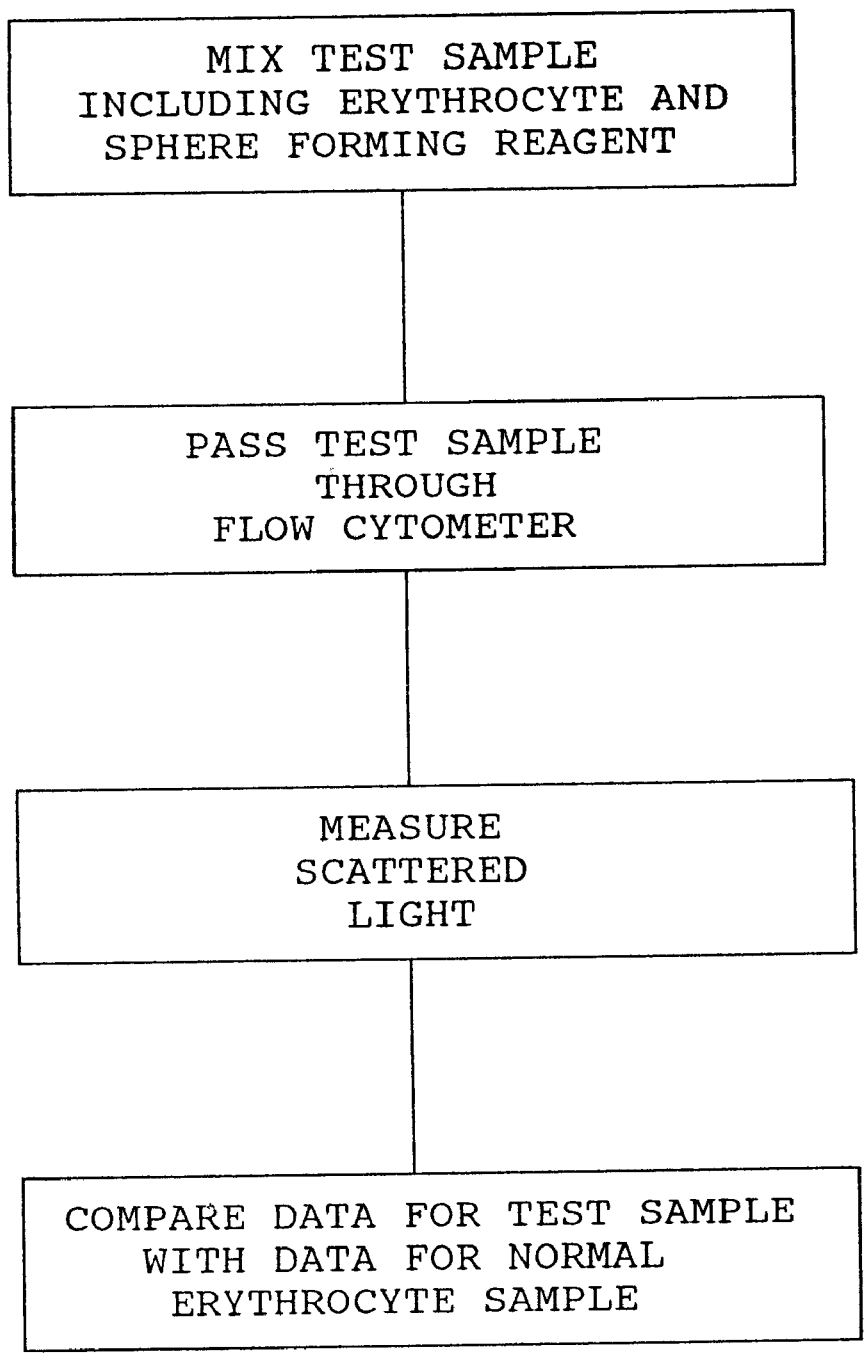
FIG. 1A is a flow diagram illustrating the method of the present invention.
Figure 4:
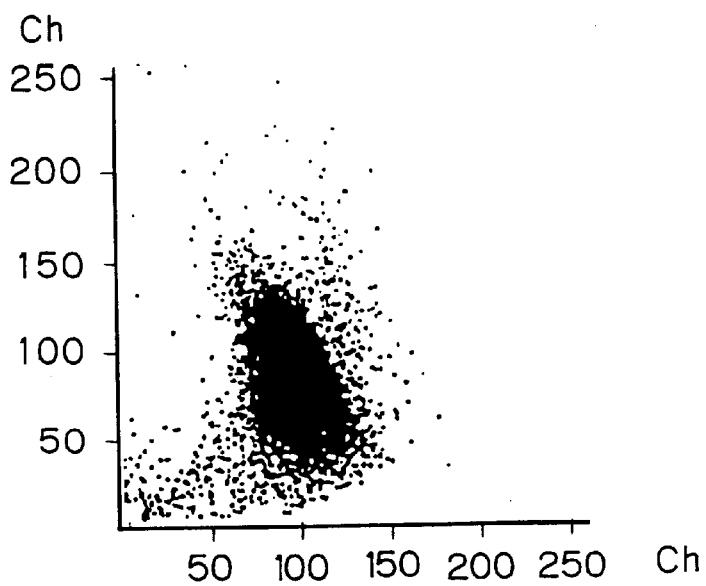
FIG. 4 is a low angle forward scattering-high angle forward scattering scattergram of elliptocytes.

The above sphere-forming reagent and a normal sample were mixed at a sample dilution ratio of 1:200. The mixture was reacted for 40 seconds at 40° C., and measured for scattered light by means of a flow cytometer using a red semiconductor laser as a light source. Based on the measurements, a high angle (8 to 20 degrees) forward scattering light histogram, and a low angle (1 to 6 degrees) forward scattering light-high angle (8 to 20 degrees) forward scattering light scattergram were prepared to determine the normal ranges. For their determinations, 60 samples were measured. An example of a normal sample is shown in FIGS. 1 and 2. As shown in FIG. 1, the high angle forward scattering light particle size distribution gave a histogram with a nearly normal distribution. In the histogram as in FIG. 1, the high angle forward scattering light was plotted on the X axis, while the relative frequency (%) is plotted on the Y axis. In the two-dimensional scattergram as in FIG. 2, the low angle forward scattering light was plotted on the X axis, while the high angle forward scattering light was plotted on the Y axis.

Detection of abnormal morphology

Samples in which elliptocytes, echinocytes, dacryocytes, schizocytes, or anisocytotic erythrocytes appeared were measured under the same conditions as described above. A high angle (8 to 20 degrees) forward scattering light histogram, and a low angle (1 to 6 degrees) forward scattering light-high angle (8 to 20 degrees) forward scattering light scattergram were prepared for each sample. The results are shown in FIGS. 3 to 12.

Figure 3:
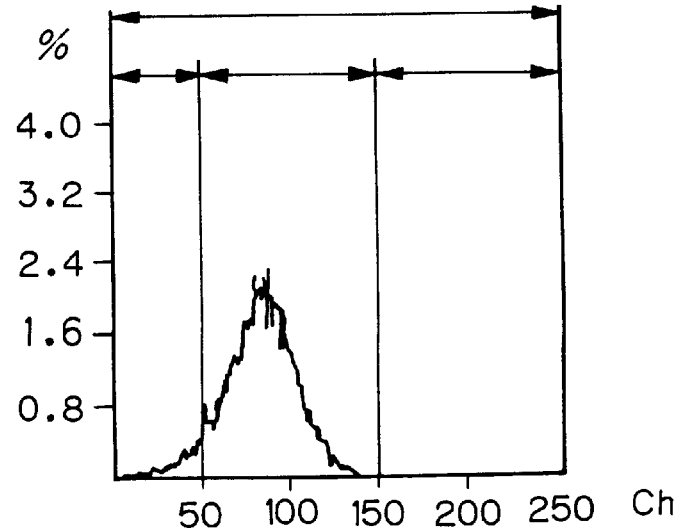
FIG. 3 is a high angle forward scattering histogram of elliptocytes.
Figure 9:
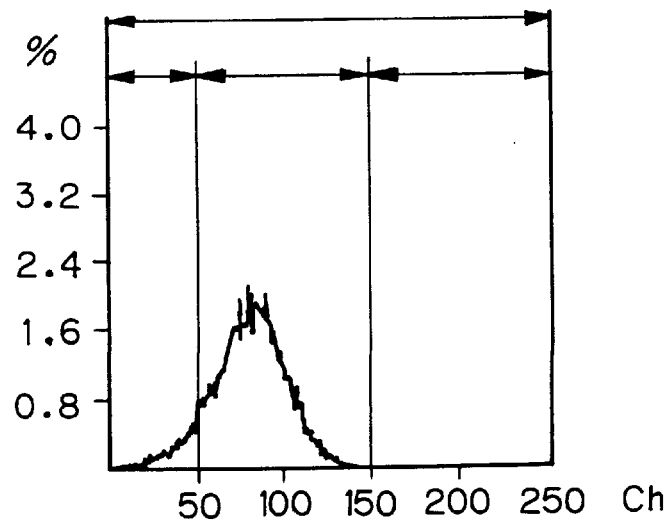
FIG. 9 is a high angle forward scattering histogram of schizocytes.
Figure 10:
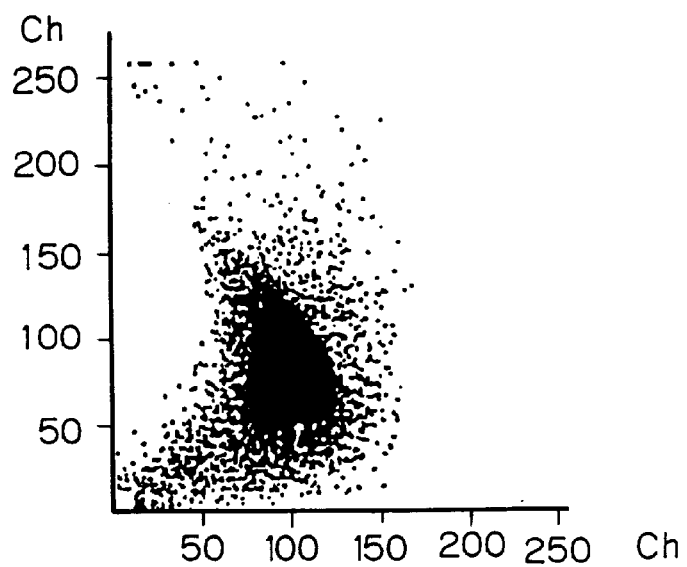
FIG. 10 is a low angle forward scattering-high angle forward scattering scattergram of schizocytes.

With elliptocytes or schizocytes, the base of the histogram spread toward lower intensities in the high angle forward scattering light particle size distribution (see FIGS. 3 and 9).

Figure 5:
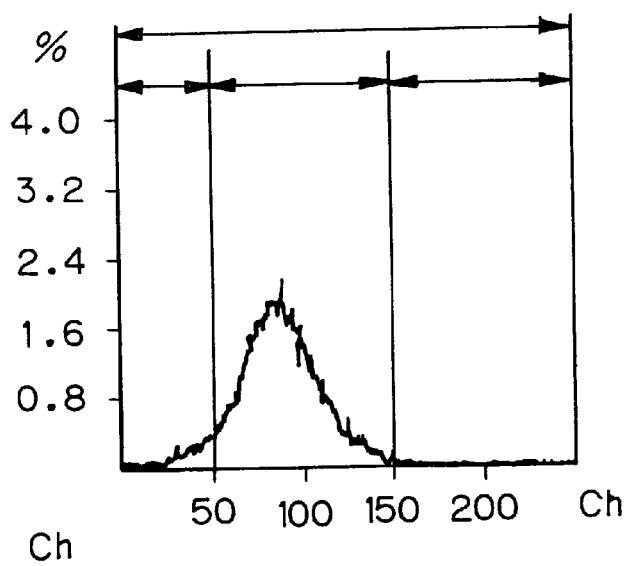
FIG. 5 is a high angle forward scattering histogram of echinocytes.
Figure 6:
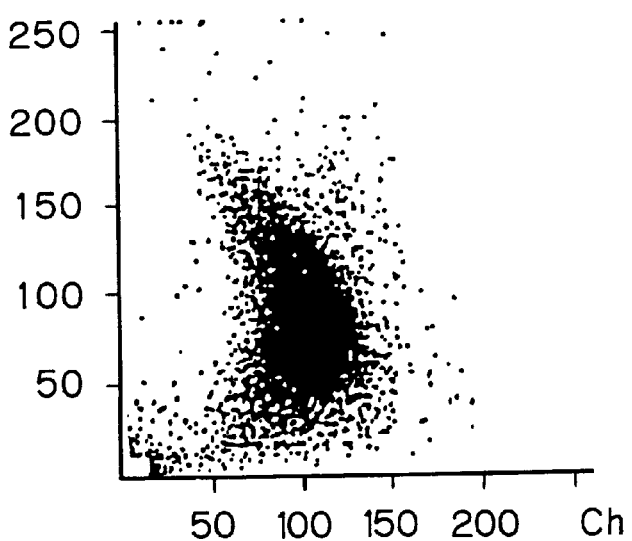
FIG. 6 is a low angle forward scattering-high angle forward scattering scattergram of echinocytes.
Figure 7:
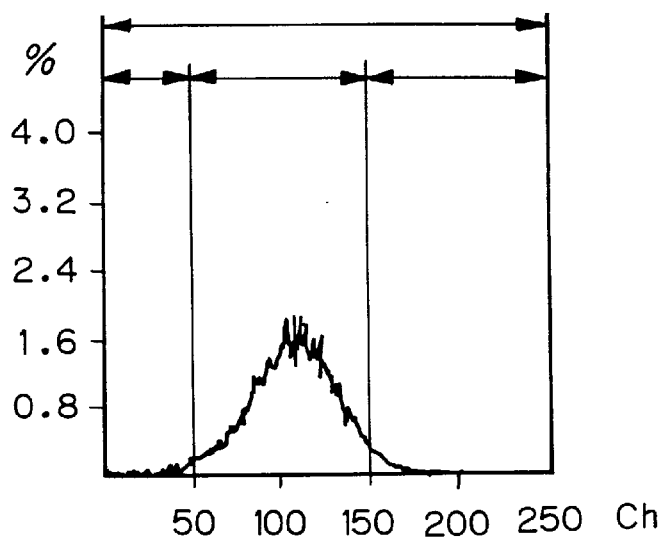
FIG. 7 is a high angle forward scattering histogram of dacryocytes.
Figure 8:
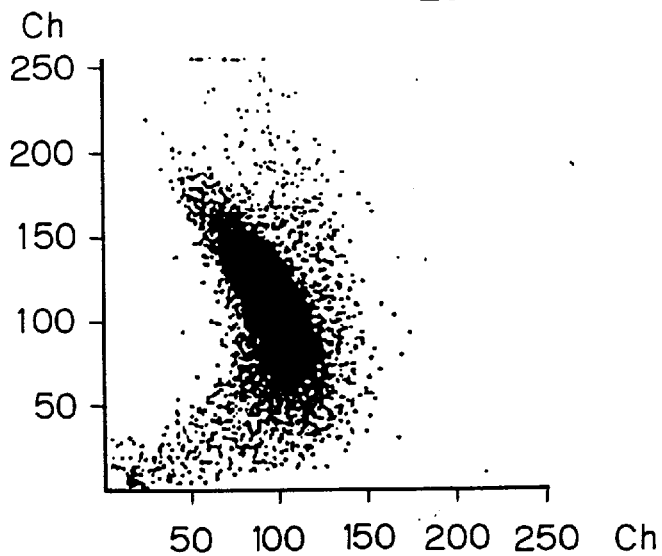
FIG. 8 is a low angle forward scattering-high angle forward scattering scattergram of dacryocytes.
Figure 11:
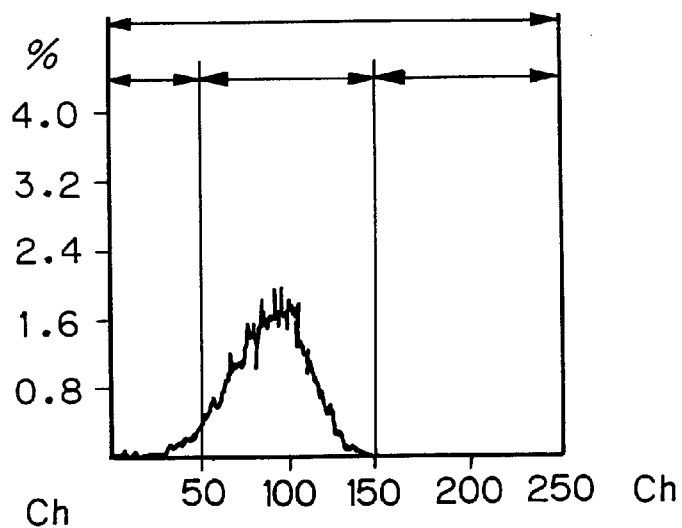
FIG. 11 is a high angle forward scattering histogram of anisocytotic erythrocytes.
Figure 12:
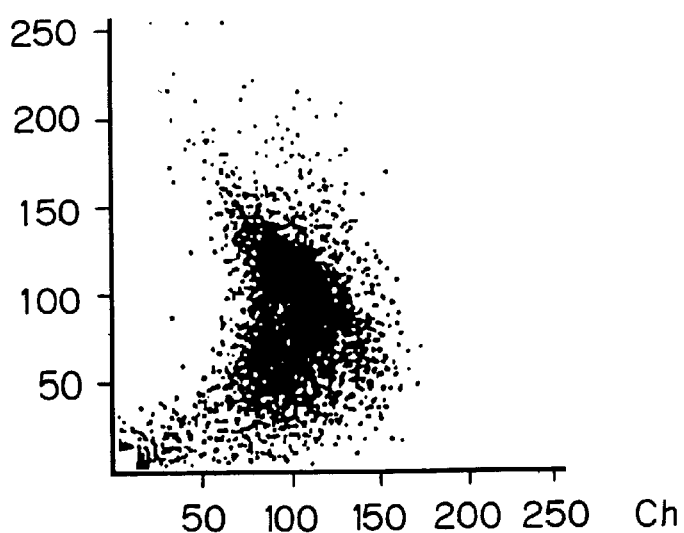
FIG. 12 is a low angle forward scattering-high angle forward scattering scattergram of anisocytotic erythrocytes.

With echinocytes, dacryocytes or anisocytotic erythrocytes, the width of the particle size distribution (standard deviation or coefficient of variation of the histogram) became larger than the normal (see FIGS. 5, 7 and 11).

According to the low angle forward scattering light-high angle forward scattering light scattergram, dots appeared in regions where few dots occur in normal samples (see FIGS. 4, 6, 8, 10 and 12).

From these data, regions where abnormal morphologies of erythrocytes appear are schematically drawn to give FIG. 13.

According to the present invention, as noted above, abnormal morphology of erythrocytes, which has thus far been undetectable, can be detected easily by the use of optical means. Thus, information for the diagnosis of various diseases can be obtained.

What is claimed is:

1. A method for detecting an abnormality in the morphology of erythrocytes, which comprises:

(1) mixing a sample containing erythrocytes with a sphere-forming reagent;

(2) introducing the sample treated in the preceding step into a detector area of a flow cytometer;

(3) measuring at least one scattered light at an angle reflecting the morphology of erythrocyte among the scattered lights emitted from the sample to obtain cell distribution data; and (4) comparing the cell distribution data with cell distribution data on normal erythrocytes that were determined beforehand.

2. The method as claimed in claim 1, wherein the angle for detection of the scattered light is 8 to 20 degrees to the optical axis.

3. The method as claimed in claim 1, wherein the angle for detection of the scattered light is 70 to 110 degrees to the optical axis.

4. The method as claimed in claim 1, further including the step of measuring scattered light at an angle reflecting the size of erythrocyte.

5. The method as claimed in claim 4, wherein the measurement of the scattered light is performed using two angles, of which the first angle reflecting the morphology of erythrocyte is 8 to 20 degrees, while the second angle reflecting the size of erythrocyte is 1 to 6 degrees.

6. The method as claimed in claim 4, wherein the measurement of the scattered light is performed using two angles, of which the first angle reflecting the morphology of erythrocyte is 70 to 110 degrees, while the second angle reflecting the size of erythrocyte is 1 to 6 degrees.

7. The method as claimed in claim 1, wherein the sphere-forming reagent contains a surfactant in an amount effective for making erythrocytes spherical without causing their lysis.

* * * * *